(12) United States Patent
Gangnus

(10) Patent No.: US 6,495,613 B1
(45) Date of Patent: Dec. 17, 2002

(54) SELF-DEFINING PLASTICS AND THE USE THEREOF IN DENTISTRY AND DENTAL TECHNOLOGY

(75) Inventor: Bernd Gangnus, Andechs (DE)

(73) Assignee: Espe Dental AG, Seefeld (DE)

( * ) Notice: Subject to any disclaimer, the term of this patent is extended or adjusted under 35 U.S.C. 154(b) by 0 days.

(21) Appl. No.: 09/623,367

(22) PCT Filed: Mar. 30, 1999

(86) PCT No.: PCT/EP99/02192

§ 371 (c)(1),
(2), (4) Date: Sep. 1, 2000

(87) PCT Pub. No.: WO99/50344

PCT Pub. Date: Oct. 7, 1999

(30) Foreign Application Priority Data

Mar. 30, 1998 (DE) ......................................... 198 14 133

(51) Int. Cl.$^7$ ................................................. A61K 6/10
(52) U.S. Cl. ...................... 523/106; 523/106; 523/122
(58) Field of Search ................................. 523/106, 122, 523/120

(56) References Cited

U.S. PATENT DOCUMENTS

| | | | |
|---|---|---|---|
| 3,830,908 A | | 8/1974 | Klippel et al. |
| 4,098,610 A | * | 7/1978 | Wexell ........................ 106/47 |
| 4,581,028 A | | 4/1986 | Fox, Jr. et al. |
| 4,612,337 A | | 9/1986 | Fox, Jr. et al. |
| 4,631,302 A | * | 12/1986 | Supcoe ....................... 523/122 |
| 4,647,601 A | | 3/1987 | McIntosh |
| 4,666,956 A | * | 5/1987 | Spielau ....................... 523/122 |
| 4,917,686 A | | 4/1990 | Bayston et al. |
| 4,933,178 A | | 6/1990 | Capelli et al. |
| 4,935,232 A | | 6/1990 | McIntosh |
| 4,973,320 A | | 11/1990 | Brenner et al. |
| 5,049,140 A | | 9/1991 | Brenner et al. |
| 5,147,686 A | * | 9/1992 | Ichimura .................... 427/217 |
| 5,344,451 A | * | 9/1994 | Dayton ........................... 23/8 |
| 5,516,480 A | | 5/1996 | Krall et al. |
| 5,585,407 A | * | 12/1996 | Patel ....................... 514/772.6 |
| 5,607,683 A | | 3/1997 | Capelli |
| 5,856,404 A | * | 1/1999 | Choung ....................... 525/127 |
| 5,866,016 A | * | 2/1999 | Jaquess ....................... 210/764 |
| 5,919,554 A | * | 7/1999 | Watterson ................... 428/201 |
| 6,030,632 A | * | 2/2000 | Sawan ........................ 424/405 |
| 6,039,965 A | * | 3/2000 | Donlan ....................... 424/405 |
| 6,054,504 A | * | 4/2000 | Toma ......................... 523/122 |
| 6,165,920 A | * | 12/2000 | Rubin ........................ 442/226 |
| 6,274,520 B1 | * | 8/2001 | Cordell ...................... 442/381 |
| 6,283,308 B1 | * | 9/2001 | Patil .......................... 210/484 |

FOREIGN PATENT DOCUMENTS

| | | |
|---|---|---|
| DE | 3725728 C2 | 2/1989 |
| DE | 3916648 C1 | 9/1990 |
| DE | 3930039 A1 | 3/1991 |
| DE | 3942112 A1 | 6/1991 |
| DE | 4226810 C1 | 1/1994 |
| DE | 4403016 A1 | 8/1995 |
| DE | 19619327 A1 | 11/1997 |
| EP | 0084407 A2 | 7/1983 |
| EP | 0360962 A2 | 4/1990 |
| EP | 0591091 A1 | 4/1994 |
| EP | 0606762 A2 | 7/1994 |
| EP | 0722660 A2 | 7/1996 |
| GB | 2210889 A | 6/1989 |
| JP | 429909 A | 1/1992 |
| WO | 9011015 A1 | 10/1990 |
| WO | 9210530 A1 | 6/1992 |
| WO | 9321970 A1 | 11/1993 |
| WO | 9414897 A1 | 7/1994 |
| WO | 9515740 A1 | 6/1995 |
| WO | 9616630 A1 | 6/1996 |
| WO | 9616631 A1 | 6/1996 |

* cited by examiner

Primary Examiner—Edward J. Cain
Assistant Examiner—James T Yeh
(74) Attorney, Agent, or Firm—Birch, Stewart, Kolasch & Birch, LLP

(57) ABSTRACT

The invention relates to modified plastics characterized in that they contain adhesion-reducing substances in such a quantity that the adhesion of microorganisms to their surface is lower by at least 50% than for non-modified plastics, and in that they contain biocidal substances in such a quantity that at least 60% of the microorganisms remaining are destroyed within 24 hours.

16 Claims, No Drawings

SELF-DEFINING PLASTICS AND THE USE THEREOF IN DENTISTRY AND DENTAL TECHNOLOGY

This application is the national phase under 35 U.S.C. § 371 of PCT International Application No. PCT/EP99/02192 which has an International filing date of Mar. 30, 1999, which designated the United States of America.

The invention relates to plastics which are self-disinfecting. The invention relates in particular to dental plastics and impression materials in which a biocidal material is incorporated and the adhesivity of whose surface vis-à-vis microorganisms is reduced.

Disinfection is a permanent requirement in dental practices and dental engineering laboratories. The transmission of germs from contaminated gloves or even bare hands via equipment, tools or materials to humans presents an enormous risk for the patient, the dentist or dental technician and their assistants. Particularly in daily procedures in practice, the patient can come into contact with contaminated items or objects, microorganisms being able to enter the blood stream through open wounds. During a session, as a result for example of using contaminated gloves when mixing an impression material and using contaminated optical conductors for the light polymerisation of radiation-curable filling materials, the risk of infection can be increased. Although the hygiene regulations are very strict, no absolutely reliable protection against infection can be guaranteed.

The use of biocidal substances is known in other fields, for example the preparation of plasticized polyvinyl chloride for use as a swimming pool cleaner, (C. R. Jones, P. S. Handley, G. D. Robson, I. M. Eastwood and M. Greenhalgh "Biocides incorporated into plasticized polyvinyl chloride reduce adhesion of Pseudomonas fluorescens BL146 and substratum hydrophobicity", Journal of Applied Bacteriology (1996) 81, 553–560). It is disadvantageous that the biocidal effect of the active ingredients 10,10-oxybisphenoxarsine (OBPA), 2-n-octyl-4-isothiazolin-3-one (OIT), 2,3,5,6-tetrachloro-4-(methylsulphonyl)pyridine (TCMP) and N-trichloromethylthiophthalimide (NCMP) introduced into the plastic comes fully into play only if the microorganisms to be destroyed come into direct contact with the surface. The reduction of adhesion necessary for this is achieved by chance by the biocidal substances used themselves.

Substances containing silver, copper or zinc also show a biocidal effect, for example DuPont products (MicroFree™ AMP). Embedded in the most varied items made from plastic, an antimicrobial effect on the surfaces of such modified plastics is noted.

Another approach is the reduction of the adhesion of proteins on surfaces. As cell membranes of microorganisms are also built up from protein components, attempts are made to prevent the accumulation of microorganisms, but particularly also of blood components, by the reduction in adhesion of proteins. An extensive state of the art describes methods for changing the properties of plastics surfaces or complete plastics parts in order to make them biocompatible. Catheters, prostheses and implants obtain biocompatible surfaces by the methods described. The deposition of biological material, for example blood cells, on prostheses or catheters or the deposition of proteins from lacrimal fluid on contact lenses can be reduced if special plastics are used for the preparation of such objects or already pre-formed objects are coated with special polymers.

WO-93/01221 describes for example polymers made from one or more radically polymerizable monomers, these polymers having groups with a permanent positive charge and groups which are able to develop a bond on surfaces.

A further approach is known from WO-94/14897, in which the biocompatibility of polymers is obtained by the coupling with polymers containing amphoteric ion groups. The amphoteric ion group is normally an ammonium salt ester; the polymer which contains this group, can be prepared via the free radical polymerisation of ethylenically unsaturated monomers together with a monomer which contains an amphoteric ion group.

Compounds which contain phosphorylcholine groups are known for their haemocompatibilizing properties and for the adhesion-reducing effect of platelets on surfaces which are treated with these compounds or have been prepared from such compounds. WO-93/21970 describes for example methods for preparing surfaces which contain groups of the general formula

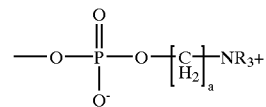

where R is the same or can be different and represents an alkyl radical with 1 to 4 C atoms and a can range from 1 to 4.

M. Humphries, J. F. Jaworzyn, J. B. Cantwell and A. Eakin described in FEMS Microbiology Letters (1987) 42, 91–101, the use of non-ionic ethoxylated and propoxylated surfactants in order to reduce the adhesion of bacteria to solid surfaces. Alcoholic ethoxylates and alkylphenolethoxylates (ICI Plastics and Petrochemicals Division, Wilton, U.K.) are used there in particular. In FEMS Microbiology Ecology (1986) 38, 299–308, M. Humphries, J. F. Jaworzyn and J. B. Cantwell described the use of biological polymers and synthetic surfactants in order to reduce the adhesion of certain bacteria species by the production of hydrophobic surfaces.

It is known however, that it is not sufficient to make the surfaces either hydrophobic or hydrophilic in order to lower the adhesion of microorganisms, as the nature of the cell walls can be completely different depending on the species.

The method of A. Pavesio, D. Renier, C. Cassinelli and M. Morra in Medical Device Technology (September 1997), 20 et seq is included in the series of coating processes, in which anti-adhesive surfaces are described by coatings with hyaluron derivatives.

More recent coating means, containing polymers with repeating units with polar or polarizable, modulating and hydrophobic fluoride-containing groups, are known from EP-0794756-A1 and EP-0794757-A1 (3M).

Preparations are also sometimes described which contain compounds which have both antimicrobial activity vis-à-vis certain bacterial strains and at the same time are intended to reduce their adhesion (Journal of Oral Rehabilitation (1988), 15, 405–411).

To summarize, the following methods are described in the state of the art:
reduction of the protein adhesion by surface treatment or by modifying the basic plastics,
destruction of the microorganisms on free surfaces by incorporated biocides.

The respective effects of these known processes are however still not satisfactory.

The object of the present invention is to prepare plastics which are improved regarding their adhesion-reducing properties or biocidal effects.

The object is achieved by specially modified plastics which are characterized in that they contain adhesion-reducing substances in such a quantity that the adhesion of microorganisms to their surface is lower by at least 50% than for non-modified plastics, and in that they contain biocidal substances in such a quantity that at least 60% of the microorganisms remaining are destroyed within 24 hours.

Permanently moist ambient conditions are present particularly in the field of dentistry. If a liquid film is located on the surface of plastics and impression materials, it is naturally permeated with proteins or microorganisms, which is extremely disadvantageous. No hopes were raised that biocidal substances would be incorporated in plastics as a result of using adhesion-reducing substances in these, as it was assumed that bacteria only briefly come into contact with the surfaces, because of the adhesion-reducing effect, at any rate too briefly for this biocidal effect to occur. Surprisingly, in spite of a clear reduction in adhesion of proteins to the surfaces of the plastics modified according to the invention, the contact time of the microorganisms with the surfaces is long enough, so that the microorganisms are predominantly destroyed.

The invention is described in detail below.

All known types of plastics can be used as plastics, depending on the modifier to be used; polyethylenes, polypropylenes, polyvinyl chlorides, polystyrenes, polycarbonates, cellophanes, cellulose acetates, polyolefins, fluorinated hydrocarbons (Teflon), polyhydroxyethyl methacrylates (PHEMA) (Hydron), polymethyl methacrylates (PMMA), polysiloxanes, polyethers and polyether silicones maybe mentioned as examples without being limitative.

A step essential to the invention is to introduce biocides into plastics. Another step essential to the invention is the incorporation of adhesion-reducing substances into the plastics or the treatment of the plastic surfaces with adhesion-reducing substances. The order of the two steps can be freely selected and is governed by the technical procedures of the manufacture of the plastics.

In order to introduce biocidal materials into the plastics, the solvent casting method is suitable for example (J. M. Schierholz, A. Rump and G. Pulverer, Arzneim. Forsch. (1997) 47, 70 et seq).

It is furthermore possible to grind the cured plastics, mix them with the biocides and press them into shape again, optionally under the action of heat. The biocide can also be added during the plastic injection process. The incorporation of biocides into dental impression materials is also conceivable. The biocide is to be added to any component of the non-cured composition. A rubber which contains biocidal properties is then obtained by the setting process. It is also advantageous with this indication that, because of the adhesion-reducing properties, blood and saliva remnants first drain off from the impression material and then microorganisms which are present are destroyed.

Substances suitable as biocides are those which release silver, silver ions, copper, copper ions, zinc or zinc ions (MicroFree™ AMP, DuPont), for example copper oxides or zinc silicates, but also the free metals. of course, all other obtainable biocides can also be used. Worthy of mention are, by way of example, ciprofloxacin-HCl (Bayer AG, Leverkusen), ciprofloxacinbetaine, 10,10-oxybisphenoxarsine, 2-n-octyl-4-isothiazolin-3-one, 2,3,5, 6-tetrachloro-4-(methylsulphonyl)pyridine, N-trichloromethylthiophthalimide, chlorohexidine, long-chained bisphenol esters (U.S. Pat. No. 3,427,345; 3M), sodium fluoride in combination with dodecylamine or other organic amines, benzalkonium chloride, cetylpyridinium chloride, 4-chloro-2-(2,4-dichlorophenoxy)phenol (Triclosan), complex or simple fluorides such as $SnF_2$, $KZnF_3$, $ZnSnF_4$, $Zn(SnF_3)_2$, potassium or zirconium hexafluorotitanate, N-oxides of saturated N-containing heterocycles substituted by quinolonecarboxylic acids or napthyridonecarboxylic acids (EP-0828715-A1). The biocides are incorporated in quantities of approx. 0.001 to 20 pts. by wt., preferably 0.01 to 10 pts. by wt., per 100 pts. by wt. of the total material.

Plastics or surfaces suitable as adhesion-reducing substances and methods for preparing adhesion-reducing plastics or surfaces are for example those based on phosphorylcholine or phosphorylethanolamine (WO-93/21970, EP-0199790-B1, WO-94/14897, WO-93/01221, EP-0641226-B1, EP-0518959-B1, WO-90/09384, EP-0157469-B1, WO-94/16749, WO-94/16748) or also those based on polyesters made from units which are derived from glycerophosphorylcholine or glycerophosphorylethanolamine and polyfunctional acids or their derivatives (EP-0275293-B1). The adhesion-reducing substances are introduced or applied as surface coating in quantities of approx. 0.05 to 50 pts. by wt., preferably 0.1 to 20 pts by wt., per 100 pts. by wt. of the total material.

Generally, the surface coating is carried out by dissolving the reactive agent in a compatible solvent, treating the surface with the solution and then drying it. Where necessary, the surface must be functionalzied; this can occur via known etching or derivatizing techniques, such as plasma discharge (see "Chemical Reactions of Polymers", Ed. E. M. Fettes (1964), Interscience, London). The diverse processes can be deduced from the previously mentioned documents, the disclosure content of which is thereby to be wholly included.

The plastics according to the invention are suitable for the preparation of plastics and plastic parts to be used in dentistry and dental engineering, for example housing parts of mixing or polymerisation equipment, also light rods of light polymerisation equipment, primary and secondary packaging materials for dental materials, application instruments for dental materials, for example for applying filling materials, as well as for dental materials themselves, for example impression materials. They are generally suitable for all plastic parts which are used when practising the dental or dental engineering profession.

The test methods and methods which are to be used to demonstrate the devitalization of microorganisms and the reduction in adhesion of microorganisms are described in the following.

TESTING METHOD 1

Vital Fluorescence Method According to Netuschil (Dtsch. Zahnärztl. Z. (1983) 38, 914–917)

The staining of live cells is carried out using fluorescein diacetate (FDA) which is absorbed by the cells and converted into fluorescein which for its part can no longer leave the cells. Dead cells can no longer carry out this reaction and therefore have to be stained with ethidium bromide (EB). This binds specifically to the DNA of the cell core which is destroyed only in the case of dead cells.

The following solutions are used as reagents:

FDA (Sigma F-5502), parent solution 5 mg/ml acetone, 2 or 6 µl per ml of physiological NaCl solution to be used each time;

EB (Sigma E-8751), parent solution, 1.25 mg/ml of physiological NaCl solution, 3 µl/ml physiological NaCl solution to be used each time.

Standardized disks are prepared to demonstrate the effect according to the invention, which on the one hand consist of plastics which were modified according to the previously described methods and on the other hand consist of non-modified plastics. These are brought into contact with a bacterial and protein suspension according to preparation example 1 (point 3) for 24 hours.

A comparison of the small sheets made from modified and non-modified plastic according to the invention is carried out after staining with FDA and EB under a light microscope by means of counting grid (Leitz Diavert with fluorescence device, 50 HBO lamp, blue and green excitation via filter block 12 or N2), the number of vital and devital microorganisms being determined by counting. A percentage value is obtained by the simple formula:

[% vital fluorescence]=100% [number of vital bacteria]/([number of vital bacteria]+[number of devital bacteria]).

PREPARATION EXAMPLE 1

Preparation of a Bacterial Suspension

Standardized small testing sheets are immersed for 4 hours in a test germ solution to examine the effect according to the invention and the number of adhered bacteria after a further 24 hours of incubation is determined.

1. Cultivation of the test germs: *Streptococcus sanguis*, biotype 1, DSM 20068 and *Streptococcus mutans*, ATCC 25175, DSM 20523 (DSM =Deutsche Sammlung von Mikroorganismen [German Microorganisms Collection]) are each cultivated in a bottle with Caso broth by incubating the inoculated broth at 30–35° C. until there is a marked turbidity. To cultivate the test germs, plates comprising Caso broth+0.5% yeast extract+1.5% agar from this broth are inoculated with 0.5 ml each and incubated for 2 to 3 days at 30–35° C.
2. Preparation of the germ suspension: The germs from overgrown plates are suspended in Ringer's solution, with the help of an inoculation loop until there is a marked turbidity. The germ suspension is subsequently treated for 10 minutes in the ultrasound bath and diluted 1:10 with synthetic saliva solution (Shellis R. P.: Archives of Oral Biology; 23, (1978), 485–489 modified according to Glenister D. A., Salamon K. E., et al.; Microbial Ecology in Health and Disease; 1, (1988), 31–38) and homogenized. The finished germ suspension contains *Streptococcus mutans* approx. $10^7$–$10^8$ CFU/ml and *Streptococcus sanguis* approx. $10^6$–$10^7$ CFU/ml.
3. Test mixture: The small test sheets are disinfected in 70% ethanol. After drying, all small sheets are transferred together into a sterile 100 ml flask using sterile tweezers and reacted with 10 ml of the germ suspension, the suspension having to be homogenized well by shaking each time before removal. Subsequently, the specimens are incubated in a shaking water bath for 4 hours at 37° C. and 100 rpm.

PREPARATION EXAMPLE 2

Preparation of an Antibiotics-containing Polyurethane (Solvent Casting)

"Walopur" polyurethane (Wolff, Walsrode) is extracted for 24 hours in a water/ethanol mixture (1:1) at 82° C. under reflux and subsequently dissolved in dimethylformamide (102° C., reflux). Ciprofloxacin-betaine is dissolved in this solution with a concentration of 750 ppm and the solvent is drawn off at 50° C. and 400 mbar over 24 hours, the residue is shaped into small sheets with 1.5 cm diameter and 0.5 mm thickness, and these are washed with deionized water and carefully dried.

PREPARATION EXAMPLE 3

Preparation of an Antibiotics-containing Plasticized Polyvinyl Chloride

For the preparation of plasticized polyvinyl chloride (pPVC) the following components are used:

| Component | parts per 100 parts resin |
|---|---|
| 571/102 Corvic (PVC resin) | 100 |
| dioctyl phthalate (plasticizer) | 25 |
| dioctyl adipate (plasticizer) | 25 |
| Lankromark LZ 935 (AKCROS) (calcium/zinc stabilizer) | 2 |
| Lankroflex Ed 6 (AKCROS) expoxidized oleate ester | 3 |
| stearic acid | 0.2 |
| calcium stearate | 0.5 |

The biocide 10, 10-oxybisphenoxarsine was introduced at 750 ppm into the pPVC formulation simultaneously with the plasticizers. The mixture was mixed in a twin-roll mill at 160° C. for 1.5 to 2 mins and laminated on a hydraulic 50-t parallel press (Moore) at 160° C. into 0.5 mm thick layers measuring 30 cm².

Small sheets measuring 1.5 cm were punched out from these layers.

PREPARATION EXAMPLE 4

Surface Coating to Reduce Adhesion

The small sheets from preparation examples 2 or 3 are immersed in an ethanol solution of prepolymerized diacetylphosphatidylcholine, prepared according to instruction A3 of WO-93/21970, removed, freed of excess material by dripping and dried at room temperature.

The effect according to the invention is clear from the following overview. Each of three small sheets made from plastic according to the invention and three small sheets made from non-modified plastic are left in the bacterial and protein solution from preparation example 1 for 24 hours after which under the light microscope analogously to method 1, the total number of bacteria on plastic according to the invention as well as the number of bacteria on non-modified plastic is ascertained, the percentage adhesion is determined from this and subsequently the number of dead and living bacteria on the plastic according to the invention are counted and the vital fluorescence is established.

Percentage values are obtained through the simple formulae:
[% adhesion]=100% [number of bacteria on plastic according to the invention]/[number of bacteria on non-modified plastic]
[% vital fluorescence]=100% [number of vital bacteria]/[number of vital bacteria]+[number of devital bacteria]

The specimens 1 to 3 represent the average values of each of three plastic small sheets according to the preparation examples 2 and 4, the specimens 4 to 6 those according to the preparation examples 3 and 4.

| Test | % adhesion | % vital fluorescence |
| --- | --- | --- |
| 1 | 49 | 5 |
| 2 | 30 | 3.7 |
| 3 | 38 | 1.2 |
| 4 | 33 | 0.05 |
| 5 | 23 | 1 |
| 6 | 19 | 0.5 |

What is claimed is:

1. A modified plastic comprising: a plastic component, adhesion-reducing substances in such a quantity that the adhesion of microorganisms to their surfaces is lower by at least 50% than for non-modified plastics, and biocidal substances in such a quantity that at least 60% of the microorganisms remaining are destroyed within 24 hours,
   wherein the biocidal substances are incorporated into the plastics, and
   wherein the adhesion-reducing substances contain phosphorylcholine, phosphorylethanolamine or polyesters made from units derived from glycerophosphorylcholine or glycerophosphorylethanolamine and polyfunctional acids or derivatives of polyfunctional acids.

2. A modified plastic according to claim 1, wherein the adhesion-reducing substances are incorporated in the modified plastic.

3. A modified plastic according to claim 1, wherein the surfaces are modified with adhesion-reducing substances.

4. A process for the preparation of a modified plastic according to claim 1, characterized in that the adhesion-reducing and biocidal substances are introduced into the modified plastic.

5. A process for the preparation of a modified plastic according to claim 1, wherein the adhesion-reducing substances are deposited on the surface of the plastic and the biocidal substances are incorporated into the plastic.

6. The modified plastic of claim 1, wherein the biocidal agent is present in an amount of 0.001 to 20 parts by weight per 100 parts by weight of the total material.

7. The modified plastic of claim 1, wherein the biocidal agent is present in an amount of 0.01 to 10 parts by weight per 100 parts by weight of the total material.

8. The modified plastic of claim 1, wherein the biocidal agent is an agent that releases silver, silver ions, copper, copper ions, zinc or zinc ions.

9. The modified plastic of claim 7, wherein the biocidal agent is a copper oxide or zinc silicate.

10. The modified plastic of claim 1, wherein the adhesion reducing substance contains phosphorus.

11. The modified plastic of claim 1, wherein the adhesion reducing substance contains diacetylphosphatidylcholine.

12. A dental product comprising a modified plastic of a plastic component, adhesion-reducing substances in such a quantity that the adhesion of microorganisms to their surfaces is lower by at least 50% than for non-modified plastics, and biocidal substances in such a quantity that at least 60% of the microorganisms remaining are destroyed within 24 hours,
    wherein the biocidal substances are incorporated into the plastics, and
    wherein the adhesion-reducing substances contain phosphorylcholine, phosphorylethanolamine or polyesters made from units derived from glycerophosphorylcholine or glycerophosphorylethanolamine and polyfunctional acids or derivatives of polyfunctional acids.

13. A dental impression composition comprising a dental substrate and a dental impression material disposed on said substrate, wherein the dental impression material is formed of a modified plastic of a plastic component, adhesion-reducing substances in such a quantity that the adhesion of microorganisms to their surfaces is lower by at least 50% than for non-modified plastics, and biocidal substances in such a quantity that at least 60% of the microorganisms remaining are destroyed within 24 hours,
    wherein the biocidal substances are incorporated into the plastics, and
    wherein the adhesion-reducing substances contain phosphorylcholine, phosphorylethanolamine or polyesters made from units derived from glycerophosphorylcholine or glycerophosphorylethanolamine and polyfunctional acids or derivatives of polyfunctional acids.

14. The dental product of claim 12, wherein said dental product is a packaging material.

15. The dental product of claim 12, wherein said dental product is a filling material.

16. The dental product of claim 12, wherein said dental product is a dental application instrument.

* * * * *